United States Patent [19]
White

[11] Patent Number: 5,681,996
[45] Date of Patent: Oct. 28, 1997

[54] ULTRASONIC DEVICE FOR INSPECTION OF METAL PARTS

[75] Inventor: Dennis A. White, Stafford Springs, Conn.

[73] Assignee: Beloit Technologies, Inc., Wilmington, Del.

[21] Appl. No.: 690,763

[22] Filed: Aug. 1, 1996

[51] Int. Cl.$^6$ .................... G01N 29/06; G01N 29/10
[52] U.S. Cl. .................... 73/622; 73/629; 73/634
[58] Field of Search .................... 73/597, 598, 620, 73/622, 623, 624, 625, 628, 633, 634, 627, 629, 637, 641, 642, 644, 599, 600

[56] References Cited

U.S. PATENT DOCUMENTS

| | | | |
|---|---|---|---|
| 3,129,581 | 4/1964 | Bande | 73/67.8 |
| 3,512,400 | 5/1970 | Lynnworth | 73/67.5 |
| 3,918,296 | 11/1975 | Kitada | 73/627 |
| 4,058,000 | 11/1977 | Ries et al. | 73/629 |
| 4,164,150 | 8/1979 | Ries et al. | 73/644 |
| 4,395,911 | 8/1983 | Macecek | 73/622 |
| 4,398,421 | 8/1983 | White | 73/597 |
| 4,472,975 | 9/1984 | Beck et al. | 73/644 |
| 4,576,048 | 3/1986 | Glenn | 73/642 |
| 4,577,505 | 3/1986 | Jestrich et al. | 73/629 |
| 4,594,897 | 6/1986 | Bantz | 73/600 |
| 4,658,649 | 4/1987 | Brook | 73/624 |
| 4,679,437 | 7/1987 | Koike et al. | 73/622 |
| 4,699,007 | 10/1987 | Kawashima et al. | 73/622 |
| 4,760,737 | 8/1988 | Kupperman | 73/622 |
| 5,161,412 | 11/1992 | John, Jr. et al. | 73/622 |
| 5,267,481 | 12/1993 | Smith | 73/623 |
| 5,383,365 | 1/1995 | Buttram | 73/598 |
| 5,421,200 | 6/1995 | Casarcia et al. | 73/632 |
| 5,492,012 | 2/1996 | Terhune | 73/598 |
| 5,497,662 | 3/1996 | Dykes | 73/634 |

OTHER PUBLICATIONS

Nondestructive Testing Handbook (2d Edition, ©1991, American Society for Nondestructive Testing, Inc. pp. 168, 254–257, 299–300, 400–401, 605–607, 864–865).

*Primary Examiner*—Michael Brock
*Assistant Examiner*—Rose M. Miller
*Attorney, Agent, or Firm*—Lathrop & Clark

[57] ABSTRACT

When an ultrasonic transducer for detecting flaws in metal plates or the wall of a metal cylinder is directed at a surface to be inspected at a particular angle, about ten percent of the signal will appear as Harris waves which propagate into the test plate at ninety degrees to the surface. This signal which propagates vertically is polarized, with the result that the signal has a greatly improved signal to noise ratio. For an incident medium of water and employing shear wave refracting in the medium of cast iron the specific angle is approximately 33 degrees from the vertical for best signal to noise ratio. For steel the specific angle is approximately 31 degrees and is about 50 degrees for brass. Shear or longitudinal waves can be employed to affect the detection of subsurface defects with the particular angle changing depending on the relation of the velocity of the sound waves in the refracting medium to the velocity of sound waves in the incident medium.

31 Claims, 3 Drawing Sheets

5,681,996

ULTRASONIC DEVICE FOR INSPECTION OF METAL PARTS

FIELD OF THE INVENTION

The present invention relates to ultrasonic instruments for nondestructive testing materials in general and for nondestructive testing of flat plates and large cylinders in particular.

BACKGROUND OF THE INVENTION

In the manufacture of tissue paper and paper towel a web of paper fibers is formed and pressed against a Yankee dryer. The web after drying is scraped from the surface of the Yankee dryer giving the web a creped texture which gives the paper it's soft absorptive characteristics. Because only a single dryer is used the Yankee dryer is normally large, typically twelve to twenty-two feet in diameter. Moreover, the Yankee dryer is heated by steam at pressures of up to 160 psig. A Yankee dryer may be 400 inches long and may have a total weight of over 100 tons. Because of its large size and high operating pressure a Yankee dryer typically has a cylindrical wall thickness of over two inches. Yankee dryers are generally formed from cast iron, e.g., Class 60, a material which has good release characteristics if the surface is properly ground. Thus the surface of a Yankee dryer requires periodic regrinding to maintain the proper surface finish.

A Yankee dryer is a pressure vessel and the safety precautions typically employed with any pressure vessel or boiler must be observed. In my previous patent U.S. Pat. No. 4,398,421 I disclosed an apparatus for measuring the thickness of a work piece which is useful for measuring the thickness steam boiler walls. Determining the wall thickness of a Yankee dryer is useful but it is also desirable to detect small voids within the thickness of the dryer wall.

Existing ultrasonic inspection systems have a limited capability for detecting small voids or finding voids in cast iron parts. Ultrasonic signals in cast iron are scattered and reflected from grain boundaries present in the cast iron. This characteristic of cast iron makes detecting small discontinuities very difficult. Even measurement of thickness in cast iron can be difficult to perform. One national study has found errors of over 40 percent in thickness measurements of cast iron with some conventional techniques.

X-ray methods are used for the inspection of Yankee dryer rolls, however x-ray methods require the use of radioactive sources which are cumbersome and dangerous. In practice x-ray images are only made of limited portions of the Yankee dryer. Furthermore, x-ray imaging does not accurately determine depth of discontinuity. Hair-line cracks are, however, typically detectable by ultrasonics.

What is needed is an apparatus and method for performing complete inspection of a Yankee dryer for material defects.

SUMMARY OF THE INVENTION

An ultrasonic transducer for detecting flaws in metal plates or the wall of a metal cylinder of this invention begins with the discovery that if an ultrasonic signal is directed at a surface to be inspected at a particular angle, about ten percent of the signal will appear as Harris waves which propagate into the test plate at ninety degrees to the surface. The signal which propagates vertically is polarized, with the result that the signal detects flaws with greatly improved signal-to-noise ratio. The particular angle is between that angle where the ultrasonic signal is refracted so as to propagate parallel to the surface of the metal plate and that angle where the ultrasonic signal is reflected by the test plate. The particular angle is measured from a normal to the surface of the plate being inspected and is greater then an angle governed by Snell's law.

$$\frac{\sin(\theta_1)}{V_1} = \frac{\sin(\theta_2)}{V_2}$$

$V_1$=velocity of the ultrasonic signal in a first medium
$V_2$=velocity of the ultrasonic signal in a second medium
$\theta_1$=angle of incidence of the ultrasonic signal, measured from a line perpendicular to the surface of the second medium
$\theta_2$=angle of refraction of the ultrasonic signal as it enters the second medium, measured from a line normal to the surface of the second medium Snell's law predicts in accord with the laws of optics, that an ultrasonic beam will be bent as it moves from a medium of lower refraction index to one of higher refraction index. In accordance with Snell's law at a selected angle of incidence of the ultrasonic signal the signal will be refracted along the surface of the solid being tested. $_2 \theta_2$ at that angle of incidence will be ninety degrees. When $_2 \theta_2$ equals 90 degrees not all the energy of the ultrasonic signal is refracted along the surface of the solid being tested. A component of about ten percent of the ultrasonic signal's power appears as a polarized signal which travels straight down from the surface and is useful for detecting flaws. This polarized or birefringent signal/beam is called a Harris wave. As the angle of incidence of the ultrasonic signal is increased the refracting signal continues to propagate along the surface of the solid until the angle of incidence is sufficiently great that the signal is totally reflected. At a selected incident angle between that required for ninety degree refraction and that required for total reflection an angle exists which produces a Harris wave which is particularly effective at detecting flaws within the surface of the solid being tested because of a high signal-to-noise ratio that is five to twenty times larger than at normal inspection angles.

For an incident medium of water and employing shear waves in the refracting medium of cast iron, the specific incident beam angle is approximately 33 degrees from the vertical. For steel, e.g., austenitic stainless steel (302), the specific angle is approximate 31 degrees and is about 50 degrees for brass. The invention can employ shear or surface waves to affect the detection of subsurface defects with the critical angle changing depending on the ratio of the velocity of the selected wave in the refracting medium to the velocity of the selected wave in the incident medium.

It is a feature of the present invention to provide a method and apparatus for detecting flaws in Yankee dryer rolls.

It is another feature of the present invention to provide a method and apparatus for detecting small voids in cast iron and other metal substrates.

It is a further feature of the present invention to provide a system for surveying the internal condition of a Yankee dryer.

Further objects, features and advantages of the invention will be apparent from the following detailed description when taken in conjunction with the accompanying drawings.

DESCRIPTION OF THE PREFERRED EMBODIMENT

Figure 4:
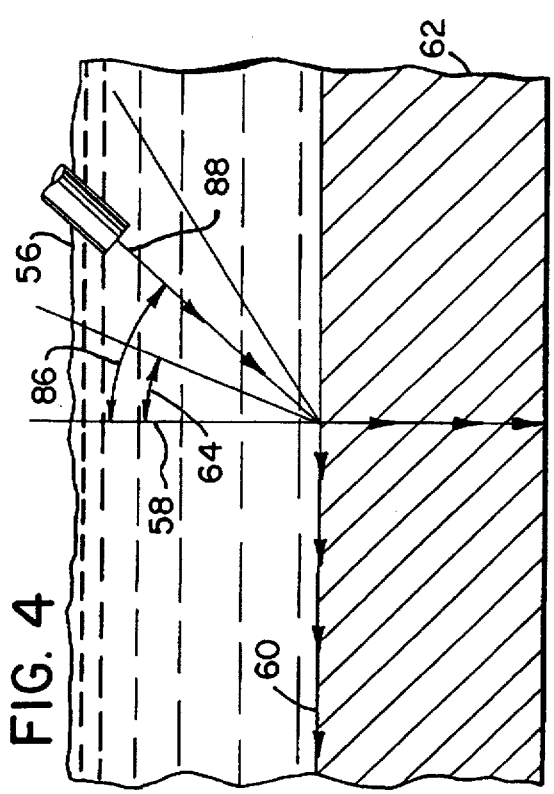
FIG. 4 is a schematic elevational front view of an ultrasonic transducer projecting an ultrasonic signal at an incidence angle of this invention which produces an ultrasonic beam which has a high signal-to-noise ratio and which penetrates normal to the surface of a solid.
Figure 5:
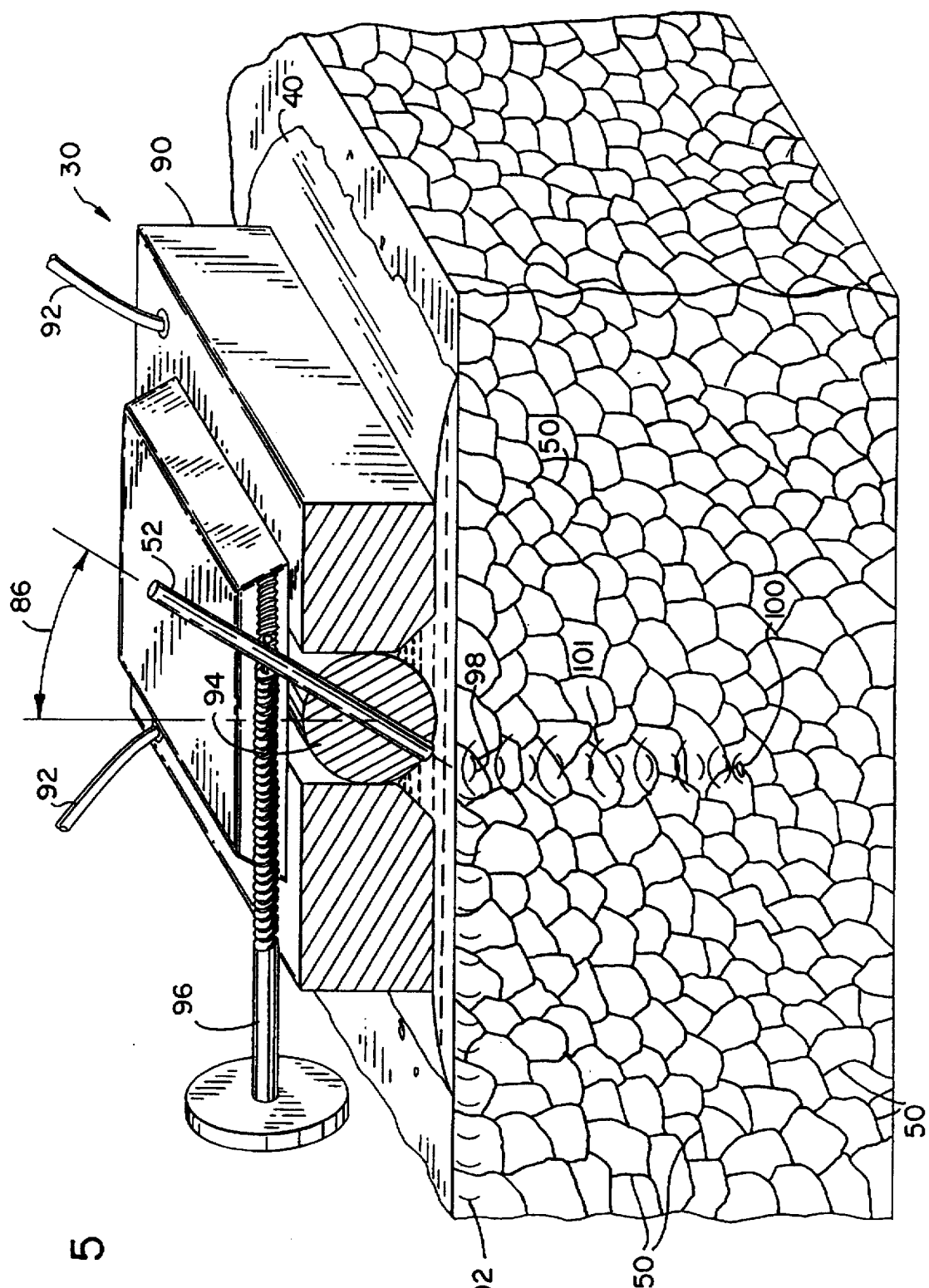
FIG. 5 is a front elevational axonometric view of an apparatus for detecting flaws in a Yankee dryer roll.
Figure 6:
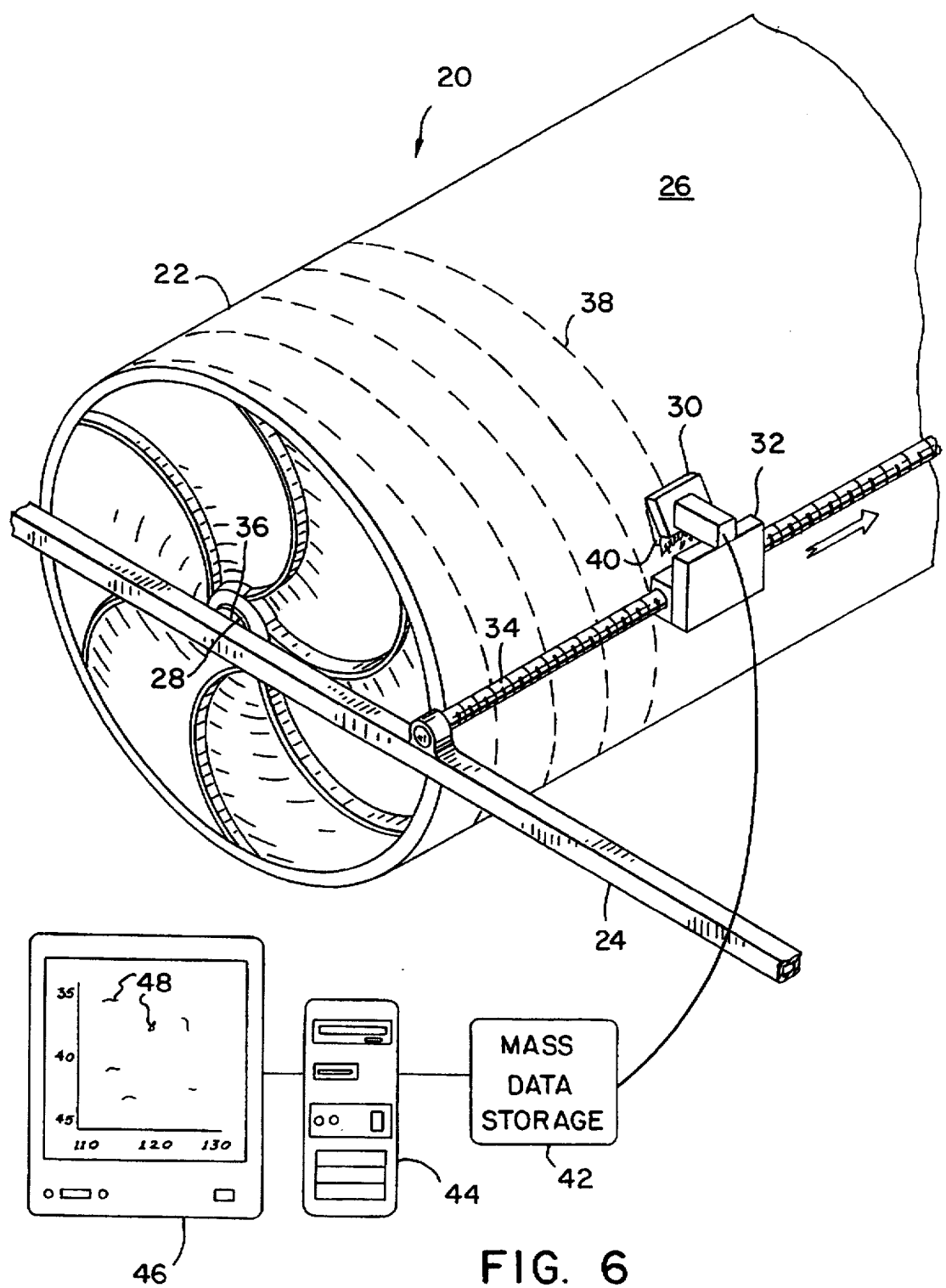
FIG. 6 is an elevational isometric view of an apparatus for scanning the surface of a Yankee dryer roll with the apparatus of FIG. 5.

Referring more particularly to FIGS. 1–6 wherein like numbers refer to similar parts an ultrasonic Yankee dryer inspection apparatus 20 is shown in FIG. 6. A Yankee dryer 22 is mounted on an inspection frame 24. The dryer 22 has a cylindrical surface 26 on which a tissue web is dried. The Yankee dryer 22 is mounted to a bearing 28 on the frame 24 and is caused to rotate by a drive mechanism (not shown). An ultrasonic transducer 30 is mounted to a crossfeed 32 which rides on a machine screw 34. The machine screw 34 is caused to rotate by a drive mechanism (not shown). The rotation of the machine screw 34 causes the crossfeed 32 with the ultrasonic transducer 30 mounted thereon to scan the surface 26 of the dryer 22 along a line parallel to the dryer axis 36. The combination of the rotary motion of the dryer 22 with the linear motion of the transducer 30, causes the transducer to describe a spiral pattern 38 on the surface of the Yankee dryer 22. The spiral pattern 38, as shown in FIG. 6, is shown widely spaced for illustrative purposes but is actually a tight spiral wherein the transducer advances along the surface 26 of the dryer 22 about ⅛ inches per revolution.

A coupling fluid 40, typically water, couples the ultrasonic energy from the transducer to the surface of the Yankee dryer 22. The output of the transducer is stored in digital format on a mass data storage device 42 such as a hard-disk or a DAT (Digital Audio Tape), etc. From the mass storage device 42 a computer 44 or oscilloscope (not shown) can process the data for display. A computer display 46 shows a plan view of the dryer 22 cylindrical surface 26 where discontinuities 48 are displayed for a selected portion of the dryer surface 26. The computer can also be used to display the amplitude of the reflected signal for a particular location. To identify the depth and length of any detected discontinuities a separate scan using conventional techniques may be required.

A conventional ultrasonic transducer employed in the conventional manner would produce data of limited utility on a device such as the inspecting apparatus 20. Conventional ultrasonic transducers produce noisy signals when used on cast iron because of the many grain boundaries 50 which cast iron contains and which reflect ultrasonic energy, limiting detection of small discontinuities. The grain boundaries 50 are illustrated in FIG. 5.

Figure 1:
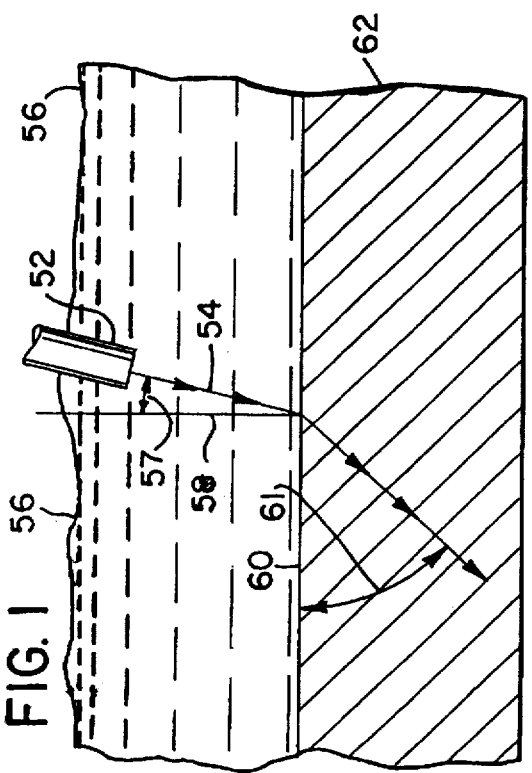
FIG. 1 is a schematic elevational view of an ultrasonic transducer projecting an ultrasonic signal through a water medium into a solid.
Figure 2:
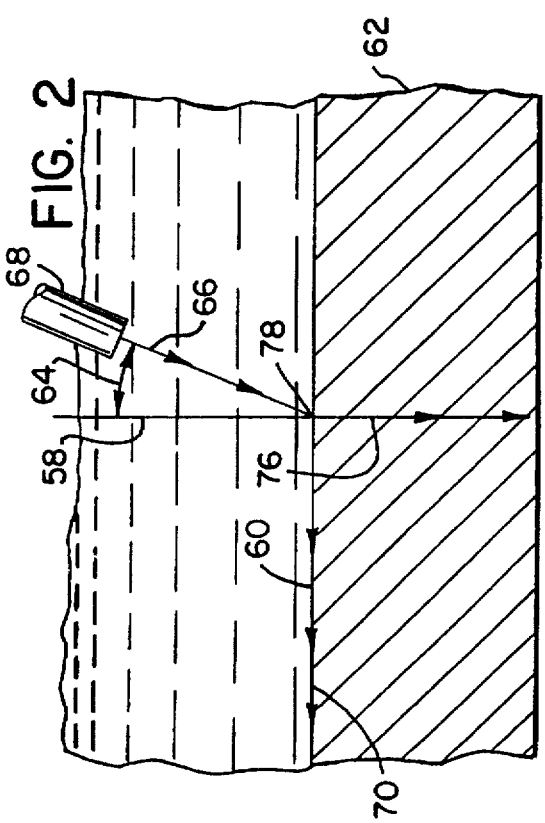
FIG. 2 is a schematic elevational view of an ultrasonic transducer projecting an ultrasonic signal at an incidence angle which causes a refracting beam to travel along the surface of a solid.

FIG. 1 illustrates an ultrasonic transducer 52 projecting a beam 54 of ultrasonic energy. The ultrasonic transducer 52 is immersed in a coupling fluid 56—typically water. The ultrasonic beam 54 is positioned at an angle 57 with respect to a reference line 58 normal to the surface 60 of a plate 62. When the ultrasonic beam 54 passes into the plate 62 it refracts at the plate surface 60 at a second angle 61 in accord with Snell's law which governs the refracting of wave energy as a wave passes from a first medium to a second medium where the second medium has a higher speed of propagation for the wave energy of interest. FIG. 2 illustrates that at a selected angle 64 an ultrasonic beam 66 from the transducer 52 will be totally refracted so that the ultrasonic beam 66 well form a beam 70 which propagates parallel to the surface 60 of the plate 62. In other words if the angle of refraction is ninety degrees so that the sine of the refracted angle is one, Snell's law may be written as:

$$\theta_1 = \arcsin\left(\frac{V_1}{V_2}\right)$$

V1=velocity of the ultrasonic signal in a first medium
V2=velocity of the ultrasonic signal in a second medium
θ1=angle of incidence of the ultrasonic signal, measured from a line perpendicular to the surface of the second medium When ultrasound is totally refracted at an interface between two media, Harris waves 76 are produced which originate from the point 78 where the beam 66 impinges on the surface 60. The Harris waves 76 propagate vertically down into the plate 62 opposite the normal line 58.

Figure 3:
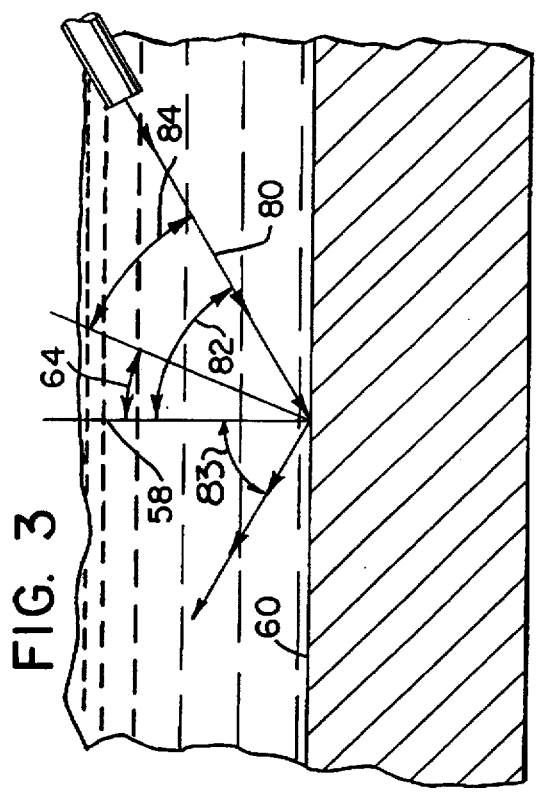
FIG. 3 is a schematic elevational view of an ultrasonic transducer projecting an ultrasonic signal at an incidence angle which causes the signal to reflect from the surface of a solid.

Harris waves 76 are produced as the angle of incidence is increased from the angle 64 governed by the above equation, until as shown in FIG. 3 the ultrasonic beam 80 is totally reflected from the surface 60 at angle of reflection 83. The location or measure of the total reflected angle 83 can be determined empirically by measuring when Harris waves are no longer produced as the angle between the transducer 52 and the normal line increases. Empirically the total reflection angle is about 120 percent of the selected angle 64 where Harris waves are first produced.

The arc 84 shown in FIG. 3 is between the selected angle 64 governed by Snell's law and the angle 82 where total reflection occurs. Harris waves 76 are produced within this arc 84. Within the arc 84 there is an angle 86 illustrated in FIG. 4 which has been found to have a very high signal-to-noise ratio, five to twenty times that of a typical ultrasonic interrogation beam. The signal-to-noise ratio may be at least 5, and can be 10 or higher. This angle 86, as shown in FIG. 4, allows detection of voids as small as one millimeter in solids such as cast iron which typically are difficult to inspect with ultrasound.

This high signal-to-noise-ratio angle 86 along which an ultrasonic beam 88 is directed, is approximately thirty-three degrees from the normal line 58 when the coupling fluid 56 is water and the plate 62 is Class 60 cast iron. For cast iron, e.g. Class 60, the shear velocity of sound is about 3,040 meters per second and the velocity of sound in water is about 1.480 meters per second. Thus in the foregoing equation the ratio of $V_1$ to $V_2$ is 0.4867 and the arcsine of the ratio is 29.1 degrees. The angle of total reflection 82 for cast iron is about 120 percent of 29.1 degrees or about 35 to 37 degrees. The optimal angle 86 generally extends to about fifty percent of the total angle enclosed by the arc 84 which for cast iron is about five to ten degrees.

The optimal angle for selected other materials where water is the coupling fluid are about 31 degrees for steel and about 50 degrees for brass. The optimal angle depends on the velocity of sound in the solid plate 62. Sound has three wave components in a rigid solid: an S or shear wave, an L or longitudinal wave, and surface wave. The velocity of sound differs for each type of sound wave and therefore the optimal angle will depend on the type of wave being utilized. While shear waves may have practical advantages, longitudinal waves can be used. As dictated by the above equations the angle where a beam of longitudinal waves are refracted to the surface of $V_2$ and propagate along the surface of the cast iron plate and also generate Harris waves is about sixteen degrees from the normal line 58.

The ultrasonic transducer 30 used to inspect a cast iron Yankee dryer 22 is shown in FIG. 5. The transducer 30 employs an ultrasonic transducer 52 mounted on a carriage block 90. The carriage block 90 has ports 92 through which water 40 or other coupling media can be supplied between the carriage block 90 and the surface 26 of a Yankee dryer 22. The ultrasonic transducer 52 is mounted in a cylinder 94 so that the angle between the transducer and the surface 26 may be adjusted. A threaded adjustment screw 96 is pivotally mounted by a universal joint which allows the screw 96 to rotate with respect to the cylinder 94. Rotation of the screw causes the angle between the transducer 52 and the surface 26 to change. FIG. 5 illustrates the way ultrasonic waves 98 penetrate into the surface of a Yankee dryer 22 and are reflected 101 off small voids 100 in the depth of the material. Also illustrated are the ultrasonic waves 102 refracted along the surface 60. Returns from the surface waves 102 can be used to detect surface roughness which is also an important characteristic of the Yankee dryer surface 26.

The ultrasonic beam or waves which penetrate 90 degrees to the surface of the Yankee dryer appear from tests conducted to be polarized, as it appears that the polarized Harris waves are effective at reducing detected scatter. Nevertheless, the exact reasons why the optimal angle has a uniquely high signal-to-noise ratio is empirically observed and is not limited to the suggested mechanism. Ultrasonic energy over a wide range has been used for ultrasonic testing upon solid materials and ultrasonic frequencies of 1 to 10 MHz in particular have been found to be effective.

It should be understood that the technique of inspecting metal objects is particularly suitable for use with cast metals in the form of smooth metal plates which term includes flat plates and the walls of large cylinders such as paper dryer rolls.

It should also be understood that the velocity of sound as used in the claims can refer to various types or components of an ultrasonic beam and thus the angle defined by the claims will depend on whether, for example, longitudinal or shear waves are selected for measuring the speed of sound.

It should be noted that although a single transducer has been indicated for both transmitting and receiving the ultrasonic signals, alternatively one transducer could be used to send, and another transducer to receive. In such a case, the sending unit would be in the position shown, whereas the receiving unit could be a position ranging from a sympathetic opposing angle to a normal angle.

It is understood that the invention is not limited to the particular construction and arrangement of parts herein illustrated and described, but embraces such modified forms thereof as come within the scape of the following claims.

It should be understood that any ultrasonic transducer frequency may be used for the invention.

I claim:

1. A method of inspecting a Yankee dryer with ultrasonics comprising the steps of:

positioning an ultrasonic transducer over a surface of a Yankee dryer;

positioning a quantity of ultrasonic coupling medium between the surface of the Yankee dryer and the transducer;

directing a first beam of ultrasonic energy from the transducer towards the surface at a selected angle from a normal to the surface, wherein the selected angle is between an angle where the beam of ultrasonic energy travels along the surface and an angle where the ultrasonic energy is reflected from the surface, thereby producing a second beam of ultrasonic energy which propagates into the Yankee dryer perpendicular to the surface;

detecting a portion of said second beam which is reflected from a defect in the Yankee dryer; and wherein the selected angle is chosen to produce a detected portion of the second beam having a signal-to-noise ratio of at least 5 to 1.

2. The method of claim 1 wherein the coupling medium is water and wherein the dryer is constructed of cast iron and wherein the selected angle is about 33 degrees from the normal to the surface.

3. The method of claim 1 wherein the coupling medium is water and wherein the dryer is constructed of steel and wherein the selected angle is about 31 degrees from the normal to the surface.

4. The method of claim 1 wherein the transducer is caused to traverse over the dryer surface and wherein the transducer generates a signal in response to the detected portion of the second beam, and said signal is recorded for a substantial portion of the traverse of the dryer surface.

5. The method of claim 4 wherein the transducer is caused to traverse the dryer surface by rotating the dryer about an axis defined by the cylindrical surface and moving the transducer along the surface of the dryer parallel to the axis so describing a helical pattern on the cylindrical surface of the dryer.

6. The method of claim 5 wherein circumferential turns of the helical pattern are spaced about one eighth of an inch apart.

7. A method for inspecting a smooth metal plate having a surface, the method comprising the steps of:

directing a beam of ultrasonic energy through a coupling medium into the surface of the metal plate, wherein the beam propagates at a first velocity through the medium, and wherein the beam propagates at a second velocity in the plate, and wherein the plate surface defines a local normal, and wherein the beam is directed at a first angle measured from the local normal, wherein a second angle with respect to the local normal is defined as the arcsine of the first velocity of the beam through the coupling medium divided by the second velocity of the beam through the plate, and wherein a third angle is defined with respect to the local normal at which the beam is substantially reflected from the plate, and wherein an arc angle is defined between the second angle and the third angle, wherein the first angle is about the second angle plus fifty percent of the arc angle; and receiving a reflected signal from the beam indicative of material discontinuities within the plate.

8. The method of claim 7 wherein the velocity of the beam through the plate used in determining the second angle is a measure of a shear wave.

9. The method of claim 7 wherein the velocity of the beam through the plate used in determining the second angle is a measure of a longitudinal wave.

10. The method of claim 7 wherein the coupling medium is water and the plate is cast iron and the first angle is thus about thirty-three degrees.

11. The method of claim 7 wherein the coupling medium is water and the plate is steel and the first angle is thus about thirty-one degrees.

12. The method of claim 7 wherein the coupling medium is water and the plate is brass and the first angle is thus about 50 degrees.

13. The method of claim 7 further comprising the step of receiving a reflected signal from a component of the beam which travels along the surface of the plate the reflected signal being indicative of the surface roughness.

14. The method of claim 7 wherein the plate is part of a cylinder defining the roll surface of a Yankee dryer.

15. The method of claim 14 wherein the transducer is caused to traverse the dryer surface by rotating the dryer about an axis defined by the cylindrical surface and moving the transducer along the surface of the cylinder parallel to the axis so describing a helical pattern on the cylindrical surface of the dryer.

16. The method of claim 15 wherein circumferential turns of the helical pattern are spaced about one eighth of an inch apart.

17. The method of claim 7 wherein the transducer is caused to traverse over the plate surface and wherein the signal from the transducer is recorded for a substantial portion of the traverse of the surface.

18. An apparatus for nondestructively testing a dryer roll for a papermaking machine, the dryer roll having an axis and a drying cylindrical surface, the apparatus comprising:

a means for mounting a dryer roll and causing it to rotate about the dryer axis;

a means for moving parallel to the dryer axis along the dryer surface;

an ultrasonic transducer mounted to the means for moving, wherein the transducer is positioned to direct a beam of ultrasonic energy into the cylindrical surface of the dryer; and a means for supplying a coupling medium between the ultrasonic transducer and the dryer surface, wherein as the transducer is moved along the dryer surface it defines a local reference line normal to the surface, and wherein the ultrasonic transducer is angled to direct the beam of ultrasonic energy through the coupling medium into the dryer surface, wherein the beam propagates through the medium at a first velocity, and through the dryer roll at a second velocity, and wherein the transducer aims the beam at a first angle measured from the local normal and wherein a second angle is defined as the arcsine of the first velocity of the beam through the coupling medium divided by the second velocity of the beam through the dryer roll, and wherein a third angle is defined at which the beam is substantially reflected from the roll, and wherein an arc angle is defined between the second angle and the third angle, wherein the first angle is about the second angle plus fifty percent of the arc angle.

19. The apparatus of claim 18 wherein the ultrasonic transducer is connected to a data storage device for receiving and storing a complete ultrasonic scan of the dryer surface.

20. The apparatus of claim 18 wherein the dryer is a Yankee dryer constructed of cast iron.

21. The apparatus of claim 18 wherein the ultrasonic transducer is adjustably mounted to the means for moving so the angle of the transducer with respect to the local normal can be adjusted.

22. A method of inspecting a metal object having a smooth surface comprising the steps of:

directing a beam of ultrasonic energy through a coupling medium into the object at a first angle from a line normal to the surface so that a portion of the ultrasonic energy propagates along the object surface and a portion of the ultrasonic energy penetrates opposite the line normal to the surface and wherein the energy penetrating opposite the line normal to the surface is polarized;

detecting energy reflected from the portion of the energy propagating along the surface to detect the surface roughness of the object, and;

detecting energy reflected from the portion penetrating opposite the line normal to the surface to detect material discontinuities within the object.

23. The method of claim 22 wherein the detected energy reflected from the penetrating portion is a shear wave.

24. The method of claim 22 wherein the detected energy reflected from the penetrating portion is a longitudinal wave.

25. The method of claim 22 wherein the coupling medium is water and the object is constructed of cast iron and the first angle is thus about thirty-three degrees.

26. The method of claim 22 wherein the coupling medium is water and the object is constructed of cast steel and the first angle is thus about thirty-one degrees.

27. The method of claim 22 wherein the coupling medium is water and the object is constructed of brass and the first angle is thus about 50 degrees.

28. The method of claim 22 wherein the object is a cylinder defining the roll surface of a Yankee dryer.

29. The method of claim 28 wherein the transducer is caused to traverse the dryer surface by rotating the dryer about an axis defined by the cylindrical surface and moving the transducer along the surface of the cylinder parallel to the axis so describing a helical pattern on the cylindrical surface of the dryer.

30. The method of claim 29 wherein circumferential turns of the helical pattern are spaced about one eighth of an inch apart.

31. The method of claim 29 wherein the traverse over the dryer surface is recorded for a substantial portion of the traverse of the surface.

* * * * *